United States Patent [19]

Trocki

[11] 4,020,103

[45] Apr. 26, 1977

[54] RECOVERY OF CALCIUM PANTOTHENATE

[75] Inventor: Julian Robert Trocki, Bayonne, N.J.

[73] Assignee: Diamond Shamrock Corporation, Cleveland, Ohio

[22] Filed: Dec. 24, 1975

[21] Appl. No.: 644,080

[52] U.S. Cl. .................................. 260/534 A
[51] Int. Cl.$^2$ ................................ C07C 99/12
[58] Field of Search ...................... 260/534 A

[56] References Cited

UNITED STATES PATENTS

| | | | |
|---|---|---|---|
| 2,390,499 | 12/1945 | Carlson et al. | 260/534 A |
| 2,848,489 | 8/1958 | Kagun | 260/534 A |

FOREIGN PATENTS OR APPLICATIONS

| | | | |
|---|---|---|---|
| 56,108 | 11/1968 | Poland | 260/534 A |

OTHER PUBLICATIONS

The Merck Index, 8th Ed. (1968), p. 240.

Elkins, "The Chemistry of Industrial Toxicology," 2nd ed. (1959), pp. 149, 150, 248, 249.

*Primary Examiner*—Joseph E. Evans
*Attorney, Agent, or Firm*—Leslie G. Nunn

[57] ABSTRACT

Calcium pantothenate is recovered from methanol solution by azeotroping the methanol with a suitable solvent. A methanol solution of calcium pantothenate is added at a regulated rate to a solvent such as octane heated above the methanol boiling point and methanol is removed by distillation as a methanol-solvent azeotrope leaving the calcium pantothenate in the form of a slurry in the azeotroping solvent. The distillation is carried out continuously but the solids may be removed continuously or collected in the still as a batch for subsequent removal.

10 Claims, No Drawings

RECOVERY OF CALCIUM PANTOTHENATE

BACKGROUND OF THE INVENTION

1. Field of the Invention:

This invention relates to recovery of calcium pantothenate from methanol solution.

2. Description of the Prior Art:

Calcium pantothenate is produced by reaction of pantolactone with the calcium salt of beta-alanine in anhydrous methanol solution. U.S. Pat. No. 2,390,499 - Carlson et al, issued Dec. 11, 1945 describes recovery of calcium pantothenate from methanol solution by recrystallization from the solution, by evaporation of the solution or by dilution of the solution with a solvent such as ether, acetone, ethyl acetate or the like which precipitates calcium pantothenate. U.S. Pat. No. 2,496,363 - Wilson et al, issued Feb. 7, 1950, teaches that precipitation of calcium pantothenate from methanol solution requires seeding of methanol solution to accelerate precipitation and that maximum separation of calcium pantothenate from solution requires allowing the solution to stand for extended periods of time. These periods of time vary from 2 to 5 days at room temperature but may be reduced by cooling the solution to 0° C and stirring during crystallization. Example I shows that the calcium pantothenate may be recovered after 2 days standing at room temperature while Example II shows that the calcium pantothenate may be removed after standing 2 days at room temperature and 1 day at 0° C.

Other procedures involving heating the solution to vaporize the methanol leaving behind a residue of solid calcium pantothenate are attended by difficulties in efficient recovery of the methanol.

Calcium pantothenate in methanol solution is reacted with calcium chloride in methanol solution to obtain a calcium chloride complex, the calcium chloride double salt of calcium pantothenate, having the following structural formula:

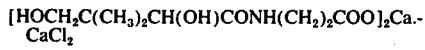
[HOCH$_2$C(CH$_3$)$_2$CH(OH)CONH(CH$_2$)$_2$COO]$_2$Ca.-CaCl$_2$

Although the double salt is somewhat hydroscopic, it remains relatively free flowing as it absorbs moisture whereas calcium panothenate readily forms a hard cake with the absorption of moisture. The complex salt has vitamin B activity which makes it suitable for use, without purification, in animal feeds or animal feed supplements. U.S. Pat. No. 2,957,025 - Brooks, issued Oct. 18, 1960, provides additional details on the complex and its use.

STATEMENT OF THE INVENTION

A mixture of about 50% by weight calcium pantothenate in methanol is added at a controlled rate to a still containing solvent heated to a temperature higher than the boiling point of methanol so that the flow rate of the calcium pantothenate - methanol mixture and the rate of heat input are balanced to evaporate the methanol as soon as it comes in contact with the hot solvent. The azeotrope of methanol vapors and solvent vapors formed by this contact are condensed and collected in a decanter where the methanol and the solvent separate allowing continuous removal of recovered methanol and continuous recycle of solvent to the still. On evaporation of methanol, calcium pantothenate precipitates as solid particles in the solvent to form a slurry of solid calcium pantothenate in the liquid azeotroping solvent.

The solvent should have a boiling point high enough to vaporize the methanol but yet be volatile enough to be easily removed from calcium pantothenate particles during subsequent processing. Further, the solvent should have little, if any, solubility in the calcium pantothenate. Methanol should have limited solubility in the solvent so that it can be easily separated from the solvent. Also, it should be non-toxic, that is, not harmful if trace amounts remaining on calcium pantothenate are ingested by animals. Useful solvents include all which form suitable azeotropes with methanol and do not create potential toxicity problems.

DESCRIPTION OF THE PREFERRED EMBODIMENTS

In the continuous recovery process, a solution of calcium pantothenate in methanol containing, e.g., about 50% solids, is pumped at a controlled rate into a still containing octane at or near its boiling point. The heated octane vaporizes the methanol and causes calcium pantothenate to precipitate and form a slurry in octane. Methanol-octane vapors leaving the still are then condensed and collected in a decanter where they separate into two liquid layers. The upper octane rich layer is returned to the still while the lower methanol rich layer is collected and removed from the decanter. If desired, the recovered methanol may be used in the preparation of another batch of calcium pantothenate solution. If desired, calcium pantothenate slurry may be removed continuously from the still and centrifuged to separate the solid and liquid. The solid is calcium pantothenate which must be dried to remove residual solvent. The liquid is clarified octane which may be returned to the still.

In the batch recovery process, a larger still is used so that all calcium pantothenate solution can be pumped into the still and the precipitated solids retained. At the completion of methanol removal the slurry of product in solvent is filtered or centrifuged to recover product.

The centrifuged calcium pantothenate contains traces of the solvent and must be dried. Drying may be carried out in any suitable dryer such as a ribbon blender where the jacket is heated to vaporize the solvent. Solvent vapors leaving the dryer may be condensed and recovered.

If the octane vapors leaving the dryer contain fine calcium pantothenate solids, these solids may be recovered by passing vapors through a dust collector, or by scrubbing the dust laden vapors with cooled octane liquid and then returning the resulting slurry to the reactor.

The azeotropic processing of a methanol solution for the removal of methanol from solids dissolved in the methanol may also be used for the recovery of solids contained in the mother liquor which results from the production of the calcium chloride complex of calcium pantothenate. The calcium chloride complex is produced by reacting pantolactone with calcium beta-alanate in a solution of calcium chloride in methanol wherein the calcium chloride complex precipitates to form a slurry. When the slurry is filtered or centrifuged to recover the calcium chloride complex, the resultant mother liquor contains some of the biologically active B vitamin. Attempts to recover the mother liquor solids without destroying the activity are unsuccessful using conventional drying methods since the mother liquor usually contains enough water to hydrolyze and thus destroy the vitamin activity during the drying. Since the azeotropic process instantaneously removes all water along with the methanol, no hydrolysis occurs and the resultant mother liquor solids recovered by azeotropic drying contain the same amount of activity which existed in the original mother liquor.

Whereas calcium pantothenate is normally made for purified pantolactone so that optimum level of biological activity (about 45%) is obtained, the cost of purifying the pantolactone adds significantly to the manufacturing cost of the calcium pantothenate. Calcium pantothenate can be produced from crude pantolactone (82–87% vs. 95% for purified) but the level of biological activity is reduced and the physical properties are adversely affected. The calcium chloride complex containing normal biological activity can be produced from less costly crude pantolactone, but more biological activity is retained and thus lost in the mother liquor than would result from the use of purified pantolactone. Thus the successful recovery of the mother liquor solids without destroying the activity improves the economics of using crude pantolactone.

The process is applicable to the recovery of D (±) calcium pantothenate, DL-calcium pantothenate as well as their corresponding calcium chloride double salts.

For a fuller understanding of the nature and objects of this invention, reference may be made to the following examples. These examples are given merely to illustrate the invention and are not to be construed in a limiting sense. All quantities, proportions and percentages are by weight and all references to temperature are ° C. unless otherwise indicated.

EXAMPLE I

A solution of calcium pantothenate was prepared by heating to reflux in one liter flask:

| | |
|---|---|
| Methanol | — 110 grams |
| Calcium beta-alanate | — 66 grams |
| Racemic pantolactone solution, 76.2% solids | — 67.5 grams |

The solution was transferred to a separatory funnel.

620 grams of octane was placed in a one liter flask equipped with stirrer, condenser, decanter and the separatory funnel containing calcium pantothenate solution. The octane was heated to reflux. The stopcock of the separatory funnel was carefully opened to allow dropwise addition of the calcium pantothenate solution. When the decanter became full, methanol was allowed to decant into a beaker and octane was allowed to return to the one liter flask. When the separatory funnel was empty, the flask was cooled and the slurry contained therein was filtered. Yield was 140 grams of wet cake which on drying gave 117 grams of calcium pantothenate.

EXAMPLE II

Charged 500 monochlorobenzene into a 2 liter glass flask equipped with agitator, inlet tube for injecting calcium pantothenate methanol solution into the flask, condenser and receiver. Heated monochlorobenzene to 90° C ± 5° C and slowly added DL-calcium pantothenate solution using a peristaltic metering pump to the hot solvent. Adjusted feed rate to avoid overloading condenser and accumulation of methanol in the flask. Methanol accumulation in the flask will cause solids to agglomerate into a doughy mass. A total of 200 g of calcium pantothenate methanol solution was added and the resulting slurry cooled and filtered to recover solid calcium pantothenate. The solid was dried in an oven at 80° C under vacuum. A total of 100 g of calcium pantothenate having normal biological activity was recovered.

EXAMPLE III

Crude racemic pantolactone, assay 81.7% was used to produce the calcium chloride complex salt of calcium pantothenate. 1890 grams of crude pantolactone containing 1625 grams of 95% quality pantolactone was reacted with 1388 grams calcium beta-alanate and 760 grams of calcium chloride in methanol. The resultant slurry of the complex in methanol was filtered to yield 2831 grams of product. The mother liquor from the filtration was azeotropically distilled to remove methanol as described in Examples I and II to recover 1072 grams of mother liquor solids. The mother liquor solids had a bioassay of 8.48%. Activity in the complex salt was $2831 \times 0.40 = 1132$ grams. Activity in the mother liquor solids was $1072 \times 0.0848 = 91$ grams. Total activity recovered was $1132 + 91 = 1223$ grams. Thus $91/1223 \times 100 = 7.4\%$ of total available activity was recovered in the mother liquor solids.

EXAMPLE IV

A four week feeding trial with broiler chickens was made to study the possible toxic effect of the octane processed calcium pantothenate. The normal growth rate and feed efficiencies obtained indicate there is no toxic effect from the use of the calcium pantothenate.

EXAMPLE V

A four week feeding trial with broiler chickens was made to evaluate octane processed calcium pantothenate made for purified pantolactone and the calcium chloride complex salt made from crude pantolactone. The normal growth rate and feed efficiencies indicate that the use of octane and the use of crude pantolactone had no toxic effects.

While the invention has been described with reference to certain specific embodiments thereof, it is understood that it is not to be so limited since alterations and changes may be made therein which are within the full and intended scope of the appended claims.

What is claimed is:

1. A process for recovery of calcium pantothenate comprising:
   Adding a mixture of calcium pantothenate in methanol to a still containing a solvent heated to a temperature above the methanol boiling point at an addition rate which balances heat input rate to the still so that methanol evaporates on contact with the hot solvent and calcium pantothenate precipitates as solid particles in the hot solvent.

2. The process of claim 1 wherein the solvent is octane.

3. The process of claim 1 wherein solid particles of calcium pantothenate are removed continuously from the still.

4. The process of claim 1 wherein solid particles of calcium pantothenate are removed once from the still.

5. The process of claim 1 wherein the mixture of calcium pantothenate in methanol mixture is a mother liquor from a calcium pantothenate calcium chloride complex process.

6. The process of claim 1 wherein the solvent is monochlorobenzene.

7. The process of claim 1 for recovery of calcium pantothenate comprising:

Adding a mixture of calcium pantothenate in methanol to a still containing a solvent heated to a temperature above the methanol boiling point at an addition rate which balances heat input rate to the still so that the methanol vaporizes on contact with the hot solvent, methanol-solvent vapors leave the still, and calcium pantothenate precipitates as solid particles in the hot solvent in the still.

8. The process of claim 7 wherein the solvent is octane.

9. The process of claim 7 wherein the solvent is monochlorobenzene.

10. The process of claim 7 wherein the mixture of calcium pantothenate in methanol mixture is a mother liquor from a calcium pantothenate calcium chloride complex process.

* * * * *